(12) United States Patent
Proksa et al.

(10) Patent No.: US 11,000,251 B2
(45) Date of Patent: May 11, 2021

(54) CT IMAGING SYSTEM AND A METHOD FOR A CT IMAGING SYSTEM

(71) Applicant: KONINKLIJKE PHILIPS N.V., Eindhoven (NL)

(72) Inventors: Roland Proksa, Neu Wulmstorf (DE); Frank Josef Pfeiffer, Unterföhring (DE); Peter Benjamin Theodor Noel, Unterföhring (DE); Thomas Baum, Unterföhring (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 43 days.

(21) Appl. No.: 16/071,513

(22) PCT Filed: Dec. 12, 2017

(86) PCT No.: PCT/EP2017/082299
§ 371 (c)(1),
(2) Date: Jul. 20, 2018

(87) PCT Pub. No.: WO2018/108849
PCT Pub. Date: Jun. 21, 2018

(65) Prior Publication Data
US 2020/0352535 A1 Nov. 12, 2020

(30) Foreign Application Priority Data
Dec. 15, 2016 (EP) ..................................... 16204310

(51) Int. Cl.
*A61B 6/00* (2006.01)
*A61B 6/03* (2006.01)
(Continued)

(52) U.S. Cl.
CPC .............. *A61B 6/505* (2013.01); *A61B 6/032* (2013.01); *A61B 6/0407* (2013.01); *A61B 6/405* (2013.01);
(Continued)

(58) Field of Classification Search
CPC ......... A61B 6/505; A61B 6/405; A61B 6/542; A61B 6/032; A61B 6/0407; A61B 6/482; A61B 6/4241; G01T 1/161
See application file for complete search history.

(56) References Cited

U.S. PATENT DOCUMENTS 5,898,753 A * 4/1999 Schick .................. G01T 1/2018
250/370.09
6,031,892 A * 2/2000 Karellas .................. A61B 6/06
250/370.09
(Continued)

FOREIGN PATENT DOCUMENTS

EP 3028636 6/2016
RU 2514110 C1 4/2014

*Primary Examiner* — Marcus H Taningco
(74) *Attorney, Agent, or Firm* — Larry Liberchuk (57) ABSTRACT

The present invention relates to a CT imaging system as well as a method for CT imaging is provided. For CT imaging, in practice a scout scan and a main scan of a human subject may be performed. It has been found that a detector signal, provided by a detector which detects the X-ray radiation during the scout scan, may be used on the one hand for determining a respective scout image and on the other hand to determine the bone mineral density of the human subject. Although the scout scan is usually primarily performed for determining the scout image, it is of advantage, if the detector used for detecting the X-ray radiation during the scout scan is formed and/or configured to detect X-ray radiation of a first energy spectrum and to detect X-ray radiation of a different, second energy spectrum. In this case, the detector can provide more precise information about the
(Continued)

scout region of the human subject and resulting therefrom in a more precise determination of the bone mineral density. Thus, while determining the scout image and/or while performing further steps, the bone mineral density may be determined, in particular as a background process step, such that the bone mineral density may be provided for further purpose.

14 Claims, 3 Drawing Sheets (51) Int. Cl.
  *A61B 6/04* (2006.01)
  *G01T 1/161* (2006.01)
(52) U.S. Cl.
  CPC ............ *A61B 6/4241* (2013.01); *A61B 6/482* (2013.01); *A61B 6/542* (2013.01); *G01T 1/161* (2013.01)

(56) References Cited

U.S. PATENT DOCUMENTS

| | | |
|---|---|---|
| 2001/0004394 A1 | 6/2001 | Siffert |
| 2002/0067799 A1* | 6/2002 | Mitchell ................ A61B 6/482 378/62 |
| 2004/0077088 A1* | 4/2004 | Charles, Jr. .......... A61B 6/4035 435/455 |
| 2004/0101087 A1 | 5/2004 | Hsieh |
| 2006/0204069 A1* | 9/2006 | Le Bras ................ A61B 6/505 382/132 |
| 2011/0150175 A1 | 6/2011 | Hsieh |
| 2013/0343519 A1 | 12/2013 | Ma |
| 2014/0086383 A1 | 3/2014 | Huwer |
| 2014/0187932 A1 | 7/2014 | Li |
| 2015/0164454 A1 | 6/2015 | Grant |
| 2015/0230765 A1 | 8/2015 | Ma |
| 2018/0164231 A1* | 6/2018 | Davis, III ............. G01N 23/04 |

* cited by examiner

CT IMAGING SYSTEM AND A METHOD FOR A CT IMAGING SYSTEM

CROSS REFERENCE TO RELATED APPLICATIONS

This application is the U.S. National Phase application under 35 U.S.C. § 371 of International Application No. PCT/EP2017/082299, filed Dec. 12, 2017, published as WO 2018/108849 on Jun. 21, 2018, which claims the benefit of European Patent Application Number 16204310.3 filed Dec. 15, 2016. These applications are hereby incorporated by reference herein.

FIELD OF THE INVENTION

The present invention relates to a CT imaging system, a method for a CT imaging system, a computer program element and a computer-readable medium.

BACKGROUND OF THE INVENTION

Generally, the abbreviation CT refers to computed tomography. A CT imaging system may relate to a radiograph CT imaging system, such as an X-ray CT imaging system. CT imaging systems are widely used in various medical institutions for two-dimensional and/or three-dimensional imaging of a region of interest of a human subject, such as coronary arteries, a lumber spine, a proximal femur or at least a part of the whole body of the human subject, to assist the clinicians to achieve a medical diagnosis of the human subject.

For the CT imaging, X-ray radiation is used to depict the interior condition and/or structure of the three-dimensional and/or non-transparent parts of the human subject to be examined. For this purpose, the human subject is often passed, at least partly, through the CT imaging system to perform a first scan, which may also be referred to as the scout scan, on the human subject to identify a region of interest of the human subject for a subsequent, second CT scan, which may also be referred to as the main scan. The scout scan provides a projection view along a longitudinal axis of the subject. However, data collected by the scout scan often do not include information sufficient for reconstruction of a three-dimensional image, since the projection data provided by the scout scan is usually collected just along the longitudinal axis of the human subject.

An excessive dose of X-ray radiation may be harmful to a human subject, since it may damage tissue and may have a carcinogenic effect. In terms of the human subject, attempts are therefore being made to reduce the exposure of X-ray radiation.

In order to reduce a repeated and potentially uncoordinated production of X-ray radiations exposed on the human subject to generate respective images, it has been suggested in document US 2014/0086383 A1 to perform an instant switching dual energy scout scan on a region of interest of the human subject by way of instant switching between a high voltage and a low voltage, and to reconstruct a material decomposition image and a mono-energetic image corresponding to a predetermined screening purpose from the collected dual energy projection data. In an example, the high voltage relates to 140 kVp and the low voltage relates to 80 kVp.

The previous explained technique however suffers from the drawback that it results in a relatively expensive CT imaging device and/or method, if an accurate and precise measurement of a bone mineral density is to be performed. In particular, motion artefacts, caused by the switching between the low voltage and the high voltage, often prevent an accurate measurement of the bone mineral density.

SUMMARY OF THE INVENTION

There may be a need for a CT imaging system and/or a respective method for CT imaging, which allows an enhanced accuracy and precision for the determination of a bone mineral density, while allowing a reduced repeated and/or potentially additional projection of X-ray radiation to a human subject for generating tomographic images.

The object of the present invention is solved by the subject-matter of each of the independent claims. Further embodiments are incorporated in the dependent claims. It should be noted that the following described aspects of the invention also apply for the method, the computer program element and the computer-readable medium, and/or vice versa.

According to a first aspect of the invention, a CT imaging system is provided. The CT imaging system comprises a source for generating X-ray radiation, a detector for detecting X-ray radiation, a control unit for controlling the source and the detector, a support device for supporting a human subject, and a processing unit coupled to the detector for receiving a detector signal from the detector, the detector signal representing detected X-ray radiation. The source and the detector are arranged opposite to each other, such that a receiving space is arranged between the source and the detector. The support device is arrangeable at the receiving space, such that X-ray radiation generated by the source transmitted through the human subject is detectable by the detector. The detector is formed and/or configured to simultaneously detect X-ray radiation of a first energy spectrum and of a different, second energy spectrum. The control unit is configured to cause a scout scan of a scout region of interest of the human subject, such that the source is operated only with a first, single X-ray tube acceleration voltage to generate X-ray radiation during the scout scan. The processing unit is configured to determine a scout image of the scout region of interest of the human subject based on a first detector signal of the detector caused by the scout scan. The control unit is configured to cause a main scan of a main region of interest of the human subject subsequently to the scout scan, such that the source is operated only with a second, single X-ray tube acceleration voltage to generate X-ray radiation during the main scan. The processing unit is configured to determine a main image of the main region of interest of the human subject based on a second detector signal of the detector caused by the main scan. The processing unit is configured to determine a bone mineral density based on the first detector signal and/or the scout image.

It is to be understood that, although the terms first, second, scout, main, etc. may be used herein to describe various features, these features should preferably not be limited by these terms. These terms may be only used to distinguish one feature from another. For example, the scout scan may be termed as a pre-scan without departing from the scope of the present invention. As used herein, the term "and/or" includes any and all combinations of one or more of the associated listed items.

It should be understood that, when an element is referred to as being "connected" or "coupled" to another element, it may be directly connected or directly coupled to the other element or it may be indirectly connected or indirectly coupled to the other element.

The CT imaging system may also be referred to as a computed tomography system, in particular an X-ray computed tomography imaging system. The source may also be referred to as an X-ray source. The detector may also be referred to as an X-ray detector. The bone mineral density may also be referred to as a bone mineral density value. The bone mineral density may be characterized in terms of and/or may represent mineral content of a bone, i.e. grams of the bone, and/or in terms of an areal bone mineral density, i.e. grams of bone/area, in particular grams of bone/cm$^2$, and/or in terms of special bone mineral density, i.e. grams of bone/volume, in particular grams of bone/cm$^3$. The scout scan may also be referred to as a first scan or a pre-scan. The main scan may also be referred to as a second scan or a diagnostic scan.

During the scout scan, the source is operated only with the first, single X-ray tube acceleration voltage and during the main scan, the source is operated only with the second, single X-ray tube acceleration voltage. As a result, a switching between two different X-ray tube acceleration voltages during a scan, namely during the scout scan or during the main scan, may be prevented. Instead, for each scan a single, respective X-ray tube acceleration voltage is provided, which may effectively prevent motion artefacts, which may otherwise occur, if the source is operated during a scan with two X-ray tube acceleration voltages switched at a, in particular high, frequency between one and the other. As an effect, the scout scan as well as the main scan may each be performed with a reduced disturbance.

As a further effect, the detector simultaneously detects X-ray radiation of a first energy spectrum and of a different, second energy spectrum. Therefore, the detector signal may be used to successfully differentiate X-ray radiation passed through a region of the human subject.

As an even further effect, the detector provides the advantage that the first and second energy spectrums are acquired simultaneously, which increases the accuracy of the detection of the X-ray radiation. This results in a more reliable detector signal and as a result thereof in a more reliable image determined based thereon. This preferably relates to the scout image and the main image. As a further effect, the more accurate first detector signal and/or the more accurate scan image results in a more accurate determination of the bone mineral density, which ensures a higher reliability.

As an even further effect, the bone mineral density may be determined as a "by-product" of a conventional CT examination, which may comprise the scout scan and the main scan.

As an even further effect, a main scan may be performed with a contrast agent provided to the human subject, which may prevent an accurate determination of a bone mineral density. However, the scout scan may be performed previous to the main scan and may therefore be performed without the contrast agent resulting in an accurate determination of the bone mineral density.

The first, single X-ray tube acceleration voltage may also be referred to as the first X-ray voltage. The second, single X-ray tube acceleration voltage may also be referred to as the second X-ray voltage.

In an example, the source comprises the X-ray tube for generating X-ray radiation. The X-ray tube may be formed and/or configured to be operated at at least one acceleration voltage, preferably at different X-ray voltages. However, the X-ray tube and/or the control unit is/are preferably configured to operate the X-ray tube just at a single X-ray tube voltage at a time at a scan, for instance at the scout scan or the main scan.

According to an exemplary embodiment of the system, the first, single X-ray tube acceleration voltage is lower than the second, single X-ray tube acceleration voltage. As an effect, the impact of X-ray radiation on the human subject may be kept as low as possible.

According to a further exemplary embodiment of the system, the first, single X-ray tube acceleration voltage is equal to the second, single X-ray tube acceleration voltage. As an effect, the complexity of the source and/or of the control unit may be reduced. Similarly, the complexity of the CT imaging system may be reduced.

According to an exemplary embodiment of the system, the processing unit is configured to determine the main region of interest of the human subject based on the first detector signal and/or the scout image. Preferably, the processing unit is configured to determine the main region, such that the main region is a sub-region of the scout region. Thus, the main region is preferably smaller than the scout region. As an effect, the impact of X-ray radiation on the human subject may be kept as low as possible.

According to a further exemplary embodiment of the system, the control unit is configured to control the source and the detector during the scout scan, such that X-ray radiation emitted by the source is provided in a single orientation towards the detector, and wherein the scout image is a two-dimensional image. The X-ray radiation emitted by the source during the scout scan may relate to a beam, in particular a cone beam, wherein the orientation of the respective X-ray radiation relates to the mean propagation direction of the X-ray radiation. As an effect, the impact of X-ray radiation on the human subject may be kept low during the scout scan.

According to a further exemplary embodiment of the system, the control unit is configured to control the source and the detector during the main scan, such that a series of X-ray radiations is emitted by the source towards the detector resulting in X-ray radiations at different orientations around a predefined axis of the human subject, wherein the processing unit is configured to determine a series of two-dimensional images corresponding to the series of X-ray radiations, and wherein the processing unit is configured to determine the main image as a three-dimensional image based on the series of two-dimensional images. With respect to the term orientation, reference is made in an analogous manner to the explanations provided above. As an effect, the three-dimensional image forming the main image allows a substantial better evaluation and an advanced diagnostic of the human subject, in particular with respect to the region of the human subject corresponding to the main region of interest of the human subject.

According to a further exemplary embodiment of the system, the detector comprises a first detector layer for detecting the first energy spectrum of X-ray radiation and a second detector layer for detecting the second energy spectrum of X-ray radiation, wherein the first detector layer is arranged above the second detector layer. In an example, each of the first detector layer and the second detector layer form an integral layer of the detector. In a further example, the first layer is arranged and/or connected directly on top of the second detector layer. In a further example, the first detector layer and the second detector layer are arranged above each other, such that the first detector layer fully overlaps or covers the second detector layer.

In an example, X-ray radiation transmitted through the human subject may be effected by the human subject resulting in an attenuation of the X-ray radiation and/or in a change of the spectral distribution of the X-ray radiation. X-ray radiation impinging on the detector associated with the first energy spectrum may be detected by the first detector layer. X-ray radiation impinging on the detector being associated with the second energy spectrum may be detected by the second detector layer.

In an example, the first detector layer and the second detector layer are formed and/or configured, such that the first energy spectrum is different from the second energy spectrum. Preferably, the first energy spectrum relates to X-ray photons with lower energy than the second energy spectrum. In an example, the first energy spectrum may be distinctively different from the second energy spectrum. In particular, the first energy spectrum may be not overlap with the second energy spectrum. According to another example, the first energy spectrum and the second energy spectrum may overlap only partly with their respective spectrums. This may result in a minimum overlap.

In an example, the first detector layer may be formed and/or configured for detecting a low energy spectrum of X-ray radiation, when the second detector layer is formed and/or configured for detecting a high energy spectrum of X-ray radiation.

As a result, the detector is formed, in particular by its first detector layer and its second detector layer, and/or configured to simultaneously detect X-ray radiation of the first energy spectrum and of the second energy spectrum.

As a further effect, X-ray radiation associated with the first energy spectrum and X-ray radiation associated with the second energy spectrum may be detected simultaneously, distinctively and/or at the same time.

As a further effect, X-ray radiation associated with the first energy spectrum and X-ray radiation associated with the second energy spectrum may be simultaneously detected at the same position of the detector. In this regard, the position may relate to a position of the detector as such, in particular to the positions of the cells of the detector, where X-ray radiation is impinging on the detector. In other words, a detector-pixel of the detector may represent a position of the detector.

As an effect, a detector signal of the detector may represent data indicating the detected X-ray radiation, wherein said data refers to position-related-data set associated with the first energy spectrum as well as to position-related-data set associated with the second energy spectrum. Both data sets are preferably position-related to each other.

As a further effect, the determination effort and/or possible errors during the determination of the bone mineral density may be reduced. This advantage may relate to the physical connection between the first detector layer and the second detector layer, and thus to the physical interrelation between a signal component of the first detector layer and a signal component of the second detector layer.

As a result, an accurate determination of the scout image, the main image and/or the bone mineral density may be provided.

According to an exemplary embodiment of the system, the detector is a photon counting detector, and wherein the detector is formed and/or configured to detect X-ray radiation of the first energy spectrum by counting photons impinging on the detector having an energy within the first energy spectrum and to detect X-ray radiation of the second energy spectrum by counting photons impinging on the detector having an energy within the second energy spectrum.

In an example, a photon counting detector comprises at least two energy counting channels. An energy counting channel may also be referred to as a bin. According to an example, the photon counting detector comprises at least one energy counting channel for each of the first and the second energy spectrum. Preferably, the photon counting detector comprises a plurality of energy counting channel for each of the first and second energy spectrums. For instance, the photon counting detector may comprise several energy counting channels for the first energy spectrum. In an analogous manner, the photon counting detector may comprise several counting channels for the second energy spectrum. By providing several energy counting channels for each of the first and second energy spectrum, the photon counting detector may be formed and/or configured to provide a high spectral resolution.

As an effect, the detector as a photon counting detector may be formed and/or configured to simultaneously detect X-ray radiation of the first and the second energy spectrum, and in particular for a plurality of position, each preferably relating to one of the channels. As a further effect, the previously explained advantages and/or effects hold for the photon counting detector in an analogous manner.

As a further effect, an accurate determination of the scout image, the main image and/or the bone mineral density may be provided.

As an even further effect, the determination effort and/or errors during the determination of the scout image, the main image and/or the bone mineral density may be reduced. This may be a result of the plurality of energy counting channels of the detector.

According to a further exemplary embodiment of the system, the processing unit is configured to determine the bone mineral density at least partly during the main scan and/or at least partly parallel during the determination of the main image.

In an example, the processing unit is configured to determine the bone mineral density as a background process step.

According to a further example, the processing unit is configured to determine the bone mineral density automatically, in particular without any user intervention.

As an effect, the bone mineral density may be determined while the main scan is performed and/or while the determination of the main image is performed. As a result, the scout image, the main image and the bone mineral density may be provided by the system for further purposes, without a need to wait for an extra time for determining the bone mineral density. Instead, the determination of the bone mineral density may be automatically performed as a background process step, in particular such that a user may access the bone mineral density at any time when reviewing the main image.

According to a further exemplary embodiment of the system, the processing unit is configured to determine the bone mineral density of the scout region of interest of the human subject.

As an effect, the bone mineral density of the scout region may represent a bone mineral density of a larger region of the human subject, as the scout region preferably relates to a respective larger region of the human subject. The bone mineral density therefore may indicate the respective condition for the scout region of the human subject. As a result, osteoporosis diagnostic and or a respective risk assessment may be performed based thereon.

As a further effect, for example for a surgical treatment of a spine degeneration, a main scan may be performed for a treatment planning. The determination of the bone mineral density of the scout region may therefore provide useful and/or in particular additional information for such a planning.

As an even further effect, for example for oncology patients, a CT scan, in particular a main scan, may be performed for a treatment monitoring. The bone mineral density may provide information useful for such a monitoring purpose. In particular, a cancer therapy may increase the risk of osteoporosis and thus the bone mineral density may be taken into account.

According to a further exemplary embodiment of the system, the processing unit is configured to determine the bone mineral density of the main region of interest of the human subject.

As an effect, the bone mineral density of the main region may indicate respective conditions, which may be taken into account when planning a surgery at the main region of interest of the human subject.

Furthermore, reference is made in an analogous manner with respect to the advantages and/or effects explained previously in an analogous manner.

According to a further exemplary embodiment of the system, the processing unit is configured to determine a T-score based on the first detector signal, the scout image and/or the bone mineral density. As an effect, a standardized value, namely the T-score, indicating a condition of a bone mineral density may be provided.

According to a further exemplary embodiment of the system, the processing unit is configured to determine, based on the first detector signal and/or the scout image, a lean soft tissue value and/or a fat value.

In an example, the processing unit is configured to determine, based on the first detector signal and/or the scout image, different fat compartments, and in particular a respective specific fat value for each of said fat compartments.

According to a further exemplary embodiment of the system, the processing unit is configured to cause a warning signal, if the bone mineral density exceeds a predefined density threshold value or a predefined density threshold value range.

Preferably, the processing unit is configured to cause the warning signal, if the bone mineral density is lower than a predefined threshold value.

According to a second aspect of the present invention, a method for CT imaging is provided. The method comprises the following steps:

a) Performing a scout scan of a scout region of interest of a human subject, such that a source for generating X-ray radiation is operated only with a first, single X-ray tube acceleration voltage to generate X-ray radiation during the scout scan, such that the respective X-ray radiation is transmitted through the scout region towards a detector for detecting X-ray radiation, wherein the detector detects simultaneously X-ray radiation of a first energy spectrum and of a different, second energy spectrum during the scout scan resulting in a first detector signal;

b) Determining a scout image of the scout region of interest of the human subject based on the first detector signal of the detector caused by the scout scan;

c) Performing a main scan of a main region of interest of a human subject subsequent to step a) and/or b), such that the source is operated only with a second, single X-ray tube acceleration voltage to generate X-ray radiation during the main scan, such that the respective X-ray radiation is transmitted through the main region towards the detector, wherein the detector detects simultaneously X-ray radiation of the first energy spectrum and of the different, second energy spectrum during the main scan resulting in a second detector signal;

d) Determining a main image of the main region of interest of the human subject based on the second detector signal of the detector caused by the main scan; and e) Determining a bone mineral density based on the first detector signal and/or the scout image.

It is to be understood that, without repeating here all explanations, examples, features, effects and/or advantages provided with reference to the system, the method of the invention is intended to be configured to carry out the method steps which the system is configured to. Thus, all the above explained examples, explanations, features, effects and/or advantages, although provided with reference to the system, are also to be intended as being provided in an analogous manner for the method. The same preferably holds in an analogous manner for the preferred embodiments of the method, which are explained hereinafter.

With respect to the order of the steps of the method it is to be noted that step a) is performed before step c). Step b) may be performed between steps a) and c), parallel to step c) and/or at least partly parallel to step c). It is further noted, that step a) is preferably performed before step b). It is further noted, that step c) is preferably performed before step d). In an example, steps b) and d) may be performed at least partly in parallel. In a further preferred example, step a) and/or step b) is/are performed before step e).

According to a preferred embodiment of the method, step e) is performed at least partly parallel to steps b), c) and/or d).

In an example, step e) is performed as a background step, preferably being performed at least partly parallel to one of the steps b), c) and/or d). For instance, step e) may be performed at least partly parallel to step c) and/or step d).

As an effect, the bone mineral density may be determined at least partly parallel to the main scan and/or the determination of the main image. As an effect, the bone mineral density may be provided not later than the determined main image.

According to a preferred embodiment of the method, the first, single X-ray tube acceleration voltage is lower than the second, single X-ray tube acceleration voltage.

According to a preferred embodiment of the method, the source and the detector are controlled during the scout scan, such that X-ray radiation emitted by the source is provided in a single orientation towards the detector, and wherein the scout image is a two-dimensional image.

According to a further preferred embodiment of the method, the source and the detector are controlled during the main scan, such that a series of X-ray radiations is emitted by the source towards the detector resulting in X-ray radiations at different orientations around a predefined axis of the human subject, wherein step d) comprises a sub-step of determining a series of two-dimensional images corresponding to the series of X-ray radiations, and wherein step d) comprises a further sub-step of determining the main image as a three-dimensional image based on the series of two-dimensional images.

According to a further preferred embodiment of the method, the determination of the bone mineral density is characterized by a determination of the bone mineral density of the scout region of interest of the human subject.

According to a further preferred embodiment of the method, the determination of the bone mineral density is characterized by determining the bone mineral density of the main region of interest of the human subject.

According to a preferred embodiment of the method, the method comprises a further step of determining a T-score based on the first detector signal, the scout scan and/or the bone mineral density.

According to a further preferred embodiment of the method, the method comprises the step of determining, based on the first detector signal and/or the scout image, a lean soft tissue value and/or a fat value.

According to a preferred embodiment of the method, the method comprises a further step of causing a warning signal, if the bone mineral density exceeds a predefined density threshold value or a predefined density value range.

According to a third aspect of the present invention, a computer program element is provided, which, when being executed by a processing unit, is adapted to perform at least the method steps according to the second aspect of the present invention as described above. Further, the computer program element may be adapted, when being executed by a processing unit, to perform a method according to at least one of the preferred embodiments of the method described above.

According to a fourth aspect of the present invention, a computer-readable medium having stored thereon a program element is provided, which, when being executed by a processing unit, is adapted to perform the method described above, at least according to the third aspect of the present invention or according to at least one of its preferred embodiments.

According to an aspect of the present invention, a CT imaging system as well as a method for CT imaging is provided. For CT imaging, it has been found that a scout scan of a scout region of a human subject is of advantage. The scout region of the human subject usually covers a large region of the human subject. This allows to investigate the structure of the human subject with regard to the scout region of the human subject. As the scout scan usually is not performed in order to provide a detailed image of the scout region of the human subject, but rather to receive just the information necessary to provide an overview, the scout scan may be performed, such that it allows the determination of a two-dimensional image based on the results of the scout scan. Accordingly, the scout scan may be performed, such that the source provides a low dose of X-ray radiation to the human subject.

However, it has been found that a detector signal, provided by a detector which detects the X-ray radiation during the scout scan, may be used on the one hand for determining a respective scout image and on the other hand to determine the bone mineral density of the human subject, preferably of the respective scout region of the human subject. Thus, the determination of the bone mineral density may also be determined based on the detector signal provided during the scout scan.

Although the scout scan is usually primarily performed for determining the scout image, it has been found of advantage, if the detector used for detecting the X-ray radiation during the scout scan is formed and/or configured to detect X-ray radiation of a first energy spectrum and to detect X-ray radiation of a different, second energy spectrum. In this case, the detector can provide, even based on the scout scan, more precise information about the scout region of the human subject and resulting therefrom a more precise determination of the bone mineral density. Thus, while determining the scout image and/or while performing further steps, the bone mineral density may be determined, in particular as a background process step, such that the bone mineral density may be provided for further purpose.

Furthermore, based on the detector signal provided by the detector during the scout scan and/or based on the scout image, a processing unit of the system may be configured to determine a main region of the human subject for further investigation.

Alternatively, the main region of the human subject may be manually determined and provided to the system via an input interface.

Further, a main scan is performed subsequently to the scout scan. Preferably, the main region of the human subject is smaller than the scout region of the subject, and in particular forms a sub-region of the scout region. Moreover, the main scan may be performed with a higher precision and/or with a higher resolution than the scout, such that the detector signal provided by the detector during the main scan represents the main region of the human subject with a higher resolution. As a result, the overall X-ray dose applied to the human subject may be limited to a minimum.

After the main scan has been performed resulting in a respective detector signal, this detector signal may be used for determining a main image representing the main region of the human subject. With regard to the bone mineral density, the bone mineral density may, at least partly, be determined in parallel to the determination of the scout image, the main scan and/or the determination of the main image. As a result, after determining the main image, also the bone mineral density may already be provided for further purpose. As a result, a clinician using the CT imaging system may be provided not only with the scout image and thereafter with the main image, but also, in particular as a "by-product", with the bone mineral density. Therefore, the clinician may simply check the bone mineral density, even if the determination of the bone mineral density may not have been a main purpose of the CT examination of the human subject. However, it provides further information to the clinician, in particular whether the human subject may be suitable for an intended medical treatment, in particular an intended surgical treatment. It should be noted that the main scan is often performed after a contrast agent has been provided to the human subject, which may prevent an accurate determination of a bone mineral density. However, the scout scan is performed prior to the main scan and thus without the contrast agent already being provided to the human subject. Therefore, the scout scan results in a detector signal as a reliable basis for an accurate determination of the bone mineral density.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
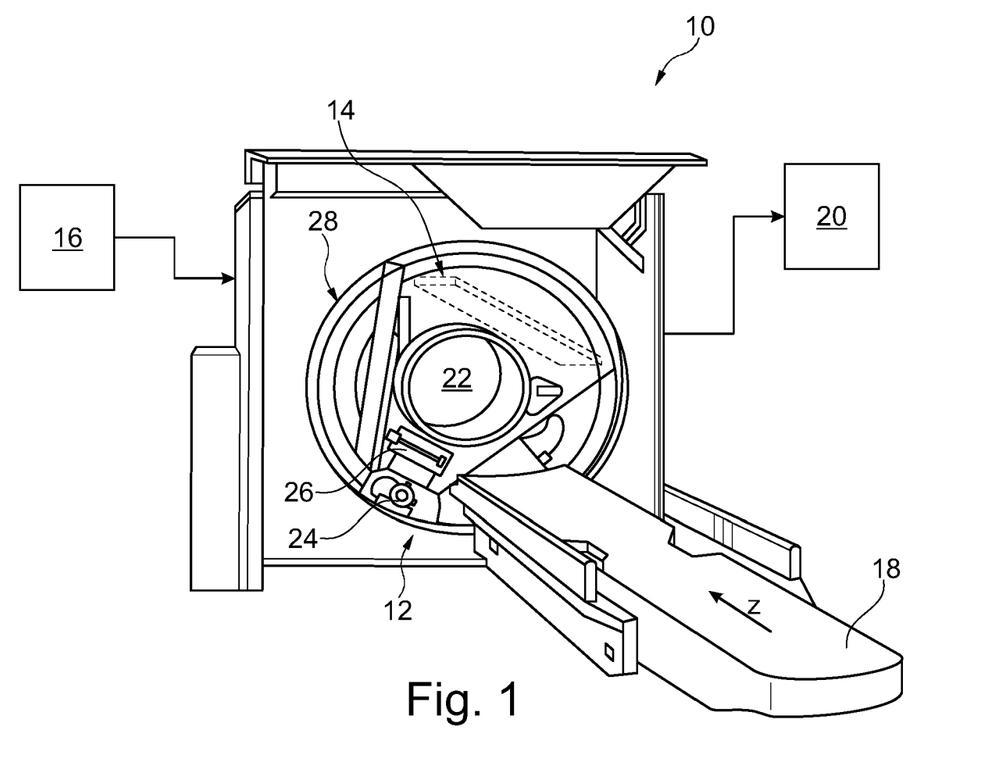
FIG. 1 schematically illustrates an example of a system.

FIG. 1 schematically illustrates an example of a CT imaging system 10. The CT imaging system 10 may be utilized to perform diagnostic scans of a region of interest of a human subject (not shown).

The CT imaging system comprises a source 12 for generating X-ray radiation. The source 12 may comprise an X-ray tube 24 and a collimator 26. The X-ray source 12 is preferably mounted to a gantry 28. The CT imaging system 10 further comprises a detector 14 for detecting X-ray radiation. The detector 14 is also preferably mounted to the gantry 28. The source 12 and the detector 14 are arranged opposite to each other. A receiving space 22 is arranged between the source 12 and the detector 14. The receiving space 22 may also be referred to as an examination region.

The CT imaging system 10 further comprises a support device 18 for supporting the human subject. The support device 18 may be a table, a couch, a chair, or the like, for supporting the human subject, such as a medical patient. The support device 18 is movable in a direction Z, preferably into and/or within the receiving space 22. The receiving space 22 is preferably defined by the gantry 28.

Furthermore, the gantry 28 is preferably formed and/or adapted as a rotatable gantry 28. Thus, the gantry 28 may be rotatable around the Z direction in order to rotate the source 12 and the detector 14 circumferentially about the receiving space 22.

The source 12 is connected to the gantry 28, such that it may project X-ray radiation towards the detector 14. Thus, the source 12 may project X-ray radiation into the object receiving space 22. If a region of a human subject is placed via the supporting device 18 into the receiving space 22, the X-ray radiation provided by the source 12 will transmit the human subject respectively and will be thereafter be detectable by the detector 14. Due to the human subject, the X-ray radiation provided by the source 12 will be subject of an attenuation and/or of a change of the spectral range.

The X-ray radiation generated by the source 12 may result from the X-ray tube 24 and thereafter collimated by the collimator 22. The collimator 22 may be a part of the source 12, too. Thus, the X-ray radiation generated by the source 12 may project a conical, wedge-, or a fan-shaped X-ray beam into the receiving space 22 and towards the detector 14.

As mentioned before, the detector 14 is preferably mounted to the gantry 28. Thus, rotating the gantry 28 may result in a simultaneous rotation movement of the source 12 and the detector 14. Accordingly, the source 12 and the detector 14 may rotate around the receiving space 22.

The CT imaging system 10 further comprises the control unit 16 for controlling the source 12 and the detector 14. The control unit 16 may also be configured for controlling a rotation or a rotation position of the gantry 28. Furthermore, the control unit 16 may be configured for controlling a movement of the support device 18, in particular such that the support device 18 may be moved into the receiving space 22. Thus, the control unit 16 may be configured to control a linear motion of the subject support 18 in the z direction and to control the source 12 and the detector 14, such that X-ray radiation is projected by the source 12 to the receiving space 22 and towards the detector 14. For scanning purposes, the subject support 12 is moved, in particular repeatedly stepped linearly, in the z direction, in order to perform a respective scan of the human subject.

The detector 14 is preferably configured to detect X-ray radiation during said scan. In particular, the detector 14 is configured to continuously detect X-ray radiation, while the support device is moved towards and/or into the receiving space 22. As a result, the detector 14 detects X-ray radiation, which has previously transmitted through the human subject.

Figure 2:
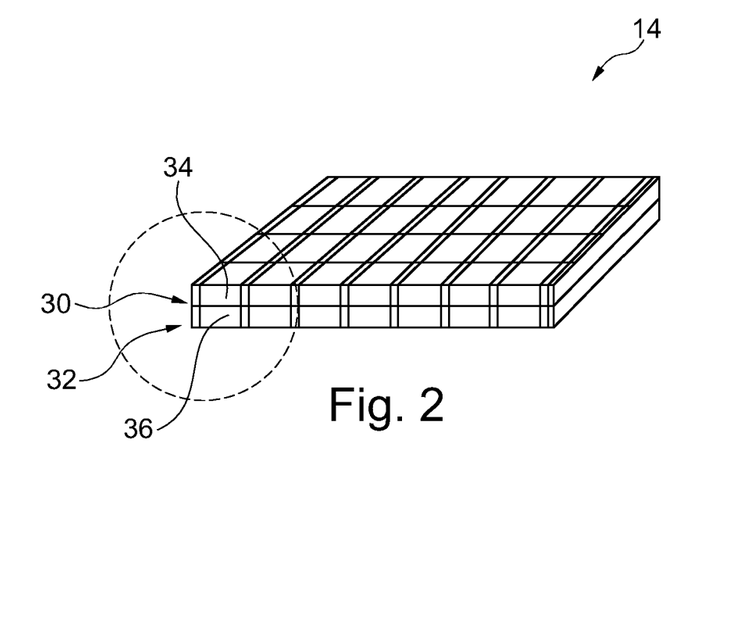
FIG. 2 schematically illustrates an example of a detector.

The detector 14 is formed and/or configured to simultaneously detect X-ray radiation of a first energy spectrum and of a different, second energy spectrum. An example of a respective detector 14 is schematically illustrated in FIG. 2. The detector 14 is preferably configured as a dual layer detector. Thus, the detector 14 preferably comprises a stack of two layers 30, 32. One of the layers 30 is arranged on top of the other layer 32. In an example, the detector 14 comprises a first detector layer 30 for detecting a first energy spectrum of X-ray radiation and a second detector layer 32 for detecting a second energy spectrum of X-ray radiation. As illustrated in FIG. 2, the first detector layer 30 is preferably arranged on top of the second detector layer 32. The first detector layer 30 is formed and/or configured to be spectral sensitive for detecting the first energy spectrum of X-ray radiation. The second detector layer 32 is formed and/or configured to be effective sensitive for detecting the second energy spectrum of X-ray radiation. For instance, the first detector layer 30 may be formed and/or for detecting a low energy spectrum of X-ray radiation, wherein the second detector layer 32 is formed and/or configured for detecting a high energy spectrum of X-ray radiation. Thus, the first energy spectrum may be lower or smaller than the second X-ray spectrum. The first and the second energy spectrum may be distinctly separated from each other or partly overlapping.

As a result, the first detector layer 30 may absorb X-ray radiation of the first energy spectrum, while the second detector layer 32 is configured to absorb X-ray radiation of the second energy spectrum. In an example, the first detector layer 30 may absorb a low X-ray energy spectrum, while the second detector layer 32 absorbs a high X-ray energy spectrum.

Preferably, each of the first and second detector layers 30, 32 comprises a plurality of cells 34, 36. The cells 34, 36 of each of the first and second detect layers 30, 32 are preferably arranged in a grid-shape. The grid of the first detector layer 30 is arranged symmetrically and/or in parallel to the grid of the second detector layer 32. As a result, each cell 34 of the first detector layer 30 is arranged on top and only above a single cell 36 of the second detector layer 32. A respective pair of cells 34, 36 of the first and second detector layers 30, 32 is circled in FIG. 2 and schematically illustrated in FIG. 3.

Figure 3:
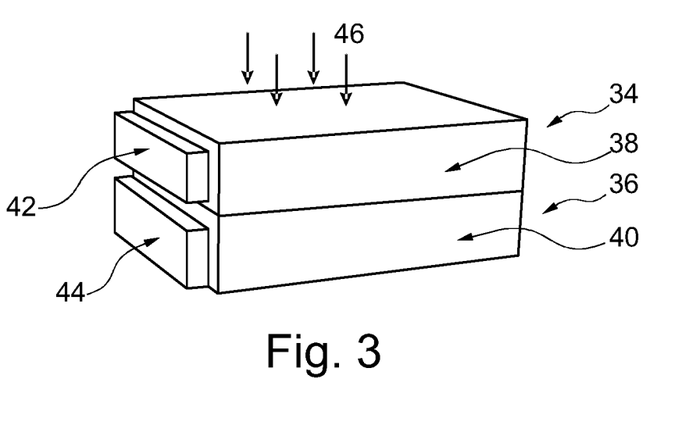
FIG. 3 schematically illustrates an example of cells of the detector.

FIG. 3 schematically illustrates the cell 34 of the first detector layer 30 being arranged on top of the cell 36 of the second detector layer 32. Each cell 34, 36 comprises a respective scintillator element 38, 40. A scintillator element 38, 40 may also be referred to as a scintillator 38, 40. Furthermore, each cell 34, 36 comprises a respective photodiode 42, 44. As schematically illustrated in FIG. 3, one of the photodiodes 42 is associated with the scintillator element 38 of the first detector layer 30, wherein the other photodiode 44 is associated with the scintillator element 40 of the second detector layer 32. The photodiode 42 is preferably attached to a side surface of the scintillator element 38. The other photodiode 44 is preferably attached to a side surface of the other scintillator element 40. However, other arrangements of the photodiodes 42, 44 with respect to their respective scintillator element 38, 40 are also possible.

If photons 46 of an X-ray radiation enter the scintillator element 38, at least a part of the photons 46 being associated with the first energy spectrum are absorbed from the scintillator element 38 resulting in light, which is sensed by the respective photodiode 42. In an analogous manner, photons 46 not being absorbed by the scintillator 38 pass through the scintillator element 38 and enter the scintillator 40, where at least a part of the photons 46 being associated with the second energy spectrum are absorbed by the scintillator element 40, resulting in light, which is sensed by the photodiode 44. As a result, each cell 34 of the first detector layer 30 is configured and formed to detect X-ray radiation of the first energy spectrum, while each cell 36 of the second detector layer 32 is formed and/or configured to detect X-ray radiation of the second energy spectrum. Therefore, the detector 14 is formed and/or configured to detect X-ray radiation of the first energy spectrum and of the different, second energy spectrum simultaneously.

As an effect, for the same position of each pair of cells 34, 36 being arranged above each other, the X-ray radiation of the first and the second energy spectrum can be detected simultaneously.

As an even further effect, the source 12 can be operated just with one X-ray tube acceleration voltage of the respective X-ray tube 24, while allowing the detection of X-ray radiation at two different energy spectrums.

As a further effect, a detector signal provided by the detector 14 represents the detected X-ray radiation of both, namely the first energy spectrum and the second energy spectrum.

It is to be noted, that the detector 14 is not limited to a configuration explained in view of the FIGS. 2 and 3. For instance, the detector 14 may be formed and/or configured as a photon counting detector. In this regard, reference is made to the explanations, features and/or effects explained previously with respect to the photon counting detector.

During a CT imaging procedure using the CT imaging system 10, two scans, namely a scout scan and a main scan, are performed. During the scout scan, the source 12 and the detector 14 preferably maintain stationary. Thus, the gantry 28 may also maintain stationary during the scout scan. For this purpose, the control unit 16 is preferably configured to control the gantry 28, such that the gantry 28 maintains in a stationary position during the scout scan. Further, during the scout scan, the human subject supported by the support device 18 is passed into and/or through the receiving space 22 in order to project X-ray radiation to a scout region of interest of the human subject. Further, the control unit 16 is configured to cause the scout scan of the scout region of interest of the human subject, such that the source 12 is operated only with the first, single X-ray tube acceleration voltage. Accordingly, the X-ray tube 24 of the source 12 is operated with the first, single X-ray tube acceleration voltage.

As a result, the source 12 generates X-ray radiation during the scout scan, wherein the X-ray radiation is projected to the receiving space 22 and transmitted through the scout region of interest of the human subject, wherein X-ray radiation transmitted through the human subject is detected by the detector 14.

In other words, the control unit 16 is preferably configured to control the source 12 and/or the detector during the scout scan, such that X-ray radiation is emitted by the source 12 to provide a single orientation towards the detector 14.

The first, single X-ray tube acceleration voltage may be between 80 kV and 140 kV. In an example, the first, single X-ray tube acceleration voltage may be 140 KV.

The detector signal provided by the detector 14 during the scout scan preferably represents a two-dimensional projection of the scout region of interest of the human subject. Said detector signal may also referred to as the first detector signal. The first detector signal is provided to the processing unit 20. The processing unit 20 is configured to determine a scout image of the scout region of interest of the human subject based on the first detector signal of the detector 14 caused by the scout scan. The scout image is preferably a two-dimensional image.

The system 10 preferably comprises a display. Furthermore, the system 10 is preferably configured to display the scout image on the display.

In an example, a clinician may review the scout image in order to identify a region within the scout image, which is of higher interest. Such a region may relate to a main region of interest of the human subject. Alternatively or additionally, the processing unit 20 may be configured to identify a main region of interest of the human subject within the scout image.

After the main region of interest of the human subject has been determined and/or provided, a main scan of the main region of interest of the human subject is performed. Thus, the main scan is performed subsequently to the scout scan. During the main scan, the main region of interest of the human subject, being supported by the supporting device 18, is passed to and through the receiving space 22, such that the source 12 projects X-ray radiation at the main region of interest of the human subject. For this purpose, the support device is preferably controlled by the control unit 16, in particular to pass the supporting device 18 stepwise into and through the receiving space 22.

During the main scan, and in particular during each step, a series of X-ray radiations is emitted by the source 12 towards the detector 14 resulting in X-ray radiations at different orientations around a predefined axis of the human subject, in particular around the z direction. Preferably, this procedure is repeated for each step. Further preferred, the processing unit 20 is configured to determine a series of two-dimensional images corresponding to the series of X-ray radiations and configured to determine a main image as a three-dimensional image based on the series of two-dimensional images.

During the main scan, the control unit 16 is configured to control the source 12, such that the source 12 is operated only with a second, single X-ray tube acceleration voltage to generate a respective X-ray radiation during the main scan. Preferably, the second, single X-ray tube acceleration voltage is between 80 kV and 140 kV. In an example, the second, single X-ray tube acceleration voltage is 140 kV. Further preferred, the second, single X-ray tube acceleration voltage is equal to the first, single X-ray tube acceleration voltage. However, the second, single X-ray tube acceleration voltage may be different from the first, single X-ray tube acceleration voltage. In particular, the first, single X-ray tube acceleration voltage may be less or lower than the second, single X-ray tube acceleration voltage.

As an effect, the impact of X-ray radiation during the scout scan can be kept as low as possible. As a result, the overall impact of X-ray radiation on the human subject can be kept as long as possible.

As noted before, the processing unit 20 is configured to determine the main image of the main region of interest of the human subject based on the second detector signal of the detector 14 caused by the main scan. Further preferred, the main image may be displayed on the display of the system 10. The system 10 may be configured accordingly. Based on the main image, a clinician may assess the main region of interest of the human subject for diagnostic purposes. This diagnosis preferably relates to a specific treatment purpose.

However, it has been found that the bone mineral density of bone material of the human subject may be of high interest, in particular for the clinician in order to provide an even advanced assessment. In order to prevent a further scan of the human subject, and in particular a further scan of the scout and/or main region of interest of the human subject, the processing unit 20 of the system 10 is configured to determine a bone mineral density based on the first detector signal (caused by the scout scan) and/or based on the scout image. The bone mineral density preferably relates to a bone mineral density value, for instance representing bone mineral contents, for instance grams of bone and/or in grams of bone/area (in particular per cm$^2$). The mineral content may relate to calcium content.

As a result, without the need of performing an additional scan of the human subject, the system 10 is configured to provide the scout image, the main image and also the bone mineral density. Thus, the bone mineral density may be determined as a "by-product" of the scout scan. As an even further effect, the bone mineral density may be provided before or at the same time of a finish of the determination of the main image. It is therefore preferred, that the processing unit 20 is configured to determine the bone mineral density at least partly during the performance of the main scan and/or at least partly parallel during the determination of the main image. Furthermore, if the bone mineral density is determined based on the first detector signal, the processing unit 20 may be configured to determine the bone mineral density at least partly parallel during the determination of the scout image. Further preferred, the processing unit 20 may be configured to determine the bone mineral density as a background process with respect to the determination of the scout image, the performance of the main scan and/or the determination of the main image. In other words, the bone mineral density may be determined via the processing unit 20 simultaneously to the determination of the scout image and/or to the determination of the main image.

Further preferred, the processing unit 20 is configured to automatically determine the bone mineral density. Thus, a clinician may take the bone mineral density into account, if required and/or helpful for the assessment, the diagnosis and/or the planning of a treatment.

Even if a surgical treatment or any other treatment is related to the main region of interest of the human subject, it may be of interest for the clinician to know the bone mineral density of a periphery region around the main region of interest. This periphery region may be covered by the scout region of interest of the human subject. In an example, the processing unit 20 is therefore configured to determine the bone mineral density of the scout region of interest of the human subject. This may provide the respective information to a clinician for an advanced diagnosis and/or treatment planning.

According to a preferred embodiment, the processing unit may be configured to determine a first bone mineral density of the scout region of interest of the human subject and to determine a second bone mineral density of the main region of interest of the human subject. As a result, both, namely the first and the second bone mineral density, may be provided for a subsequent assessment.

Furthermore, the processing unit 20 is preferably configured to cause a warning signal, if the bone mineral density exceeds a predefined density threshold value or a predefined density threshold value range. For instance, if the bone mineral density is lower than a predefined minimum density threshold value, the processing unit may cause the warning signal. The system 10 may be configured to acoustically or visually release the warning signal. For instance, the system 10 may be configured to display an item on the display representing the warning signal. As a result, a clinician who may assess the main image may be notified of the bone minimal density, which is lower than the predefined minimum density threshold value. As a result, the clinician may consider the bone mineral density for the assessment and/or for the treatment planning.

Figure 4:
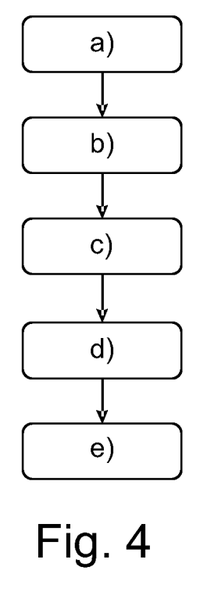
FIG. 4 schematically illustrates an example of a method.

FIG. 4 schematically illustrates an example of the method for CT imaging. The method comprises the following steps:

In a first step a), a scout scan of a region of interest of the human subject is performed, such that a source 12 for generating X-ray radiation is operated only with a first, single, X-ray tube acceleration voltage to generate X-ray radiation during the scout scan, such that the respective X-ray radiation is transmitted through the scout region towards the detector 14 for detecting X-ray radiation, wherein the detector 14 detects simultaneously X-ray radiation of a first energy spectrum and of a different, second energy spectrum during the scout scan resulting in a first detector signal.

In a second step b), a scout image of the scout region of interest of the human subject is determined based on the first detector signal of the detector 14 caused by the scout scan.

In a third step c), a main scan of the main region of interest of the human subject is performed subsequently to step a) and/or b), such that the source 12 is operated only with a second, single X-ray tube acceleration voltage to generate X-ray radiation during the main scan, such that the respective X-ray radiation is transmitted through the main region towards the detector 14, wherein the detector detects simultaneously X-ray radiation of the first energy spectrum and of the different, second energy spectrum during the main scan resulting in a second detector signal.

During a fourth step d), a main image of the main region of interest of the human subject is determined based on the second detector signal of the detector 14 caused by the main scan.

In a fifth step e), a bone mineral density is determined based on the first detector signal and/or based on the scout image.

It is understood that, without repeating here all the explanations, examples, features, effects and/or advantages provided with reference to the device 10, the method of the invention is intended to be configured to carry out the method steps for which the system 10 is configured to. Thus, all the above examples, explanations, features, effects and/or advantages, although provided previously with reference to the system 10, are also to be intended as being provided in an analogous manner for the method.

Figure 5:
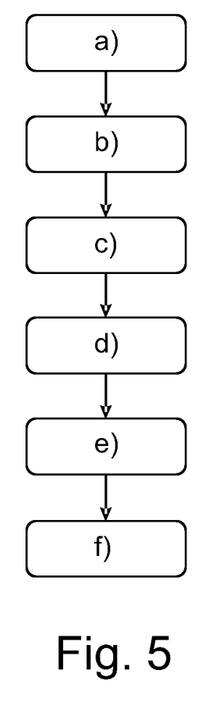
FIG. 5 schematically illustrates a further example of a method.

FIG. 5 shows an exemplary embodiment of the method. The method as schematically indicated in FIG. 5 comprises the steps a) to e), which have been previously explained with reference to FIG. 4. Thus, reference is made to the previous explanation with regard to FIG. 4. The method further comprises the sixth step f). In the sixth step f), a warning signal is determined, if the bone mineral density exceeds a predefined density threshold value and/or a predefined density threshold value range.

According to a further example of the present invention, a computer program element is provided, which, when being executed by a processing unit is adapted to carry out the method described above.

According to further example of the present invention, a computer readable medium having stored thereon a program element is provided, which, when being executed by a processing unit is adapted to carry out the method described above.

The computer program element might be stored on a computer unit, which might also be part of an embodiment of the system of the present invention. This computing unit may be adapted to perform or induce a performing of the steps of the method described above. Moreover, it may be adapted to operate the components of the above described system. The computing unit may be adapted to operate automatically and/or to execute the orders of a user. A computer program may be loaded into a working memory of a data processor. The data processor may thus be equipped to carry out the method of the invention.

It has to be noted that embodiments of the invention are described with reference to different subject matters. In particular, some embodiments are described with reference to a system whereas other embodiments are described with reference to the method. However, a person skilled in the art will gather from the above that, unless otherwise notified, in addition to any combination of features belonging to one subject matter also any combination between features relating to different subject matters is considered to be disclosed with this application. However, all features may be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments may be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single detector or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A CT imaging system, comprising:
   a source for generating X-ray radiation;
   a detector for detecting X-ray radiation;
   a control unit for controlling the source and the detector-;
   a support device for supporting a human subject; and
   a processing unit coupled to the detector for receiving a detector signal from the detector representing detected X-ray radiation;
   wherein the source and the detector are arranged opposite to each other, such that a receiving space is arranged between the source and the detector;
   wherein the support device is arrangeable at the receiving space, such that X-ray radiation generated by the source transmitted through the human subject is detectable by the detector;
   wherein the detector is formed and/or configured to simultaneously detect X-ray radiation of a first energy spectrum and of a different, second energy spectrum;
   wherein the control unit is configured to cause a scout scan of a scout region of interest of the human subject, such that the source is operated only with a first, single X-ray tube acceleration voltage to generate X-ray radiation during the scout scan;
   wherein the processing unit is configured to determine a scout image of the scout region of interest of the human subject based on a first detector signal of the detector caused by the scout scan;
   wherein the control unit is configured to cause a main scan of a main region of interest of the human subject subsequently to the scout scan, such that the source is operated only with a second, single X-ray tube acceleration voltage to generate X-ray radiation during the main scan;
   wherein the processing unit is configured to determine a main image of the main region of interest of the human subject based on a second detector signal of the detector caused by the main scan; and
   wherein the processing unit is configured to determine a bone mineral density based on the first detector signal and/or the scout image.

2. The system according to claim 1, wherein the first, single X-ray tube acceleration voltage is lower than the second, single X-ray tube acceleration voltage.

3. The system according to claim 1, wherein the control unit is configured to control the source and the detector during the scout scan, such that X-ray radiation emitted by the source is provided in a single orientation toward the detector, and wherein the scout image is a two-dimensional image.

4. The system according to claim 1, wherein the control unit is configured to control the source and the detector during the main scan, such that a series of X-ray radiations is emitted by the source toward the detector resulting in X-ray radiations at different orientations around a predefined axis of the human subject, wherein the processing unit is configured to determine a series of two-dimensional images corresponding to the series of X-ray radiations, and wherein the processing unit is configured to determine the main image as a three-dimensional image based on the series of two-dimensional images.

5. The system according to claim 1, wherein the detector comprises a first detector layer for detecting the first energy spectrum of X-ray radiation and a second detector layer for detecting the second energy spectrum of X-ray radiation, the first detector layer is arranged above the second detector layer.

6. The system according to claim 1, wherein the detector is a photon counting detector, and wherein the detector is formed and/or configured to detect X-ray radiation of the first energy spectrum by counting photons impinging on the detector having an energy within the first energy spectrum and to detect X-ray radiation of the second energy spectrum by counting photons impinging on the detector having an energy within the second energy spectrum.

7. The system according to claim 1, wherein the processing unit is configured to determine the bone mineral density at least partly parallel during the main scan and/or the determination of the main image.

8. The system according to claim 1, wherein the processing unit is configured to determine the bone mineral density of the scout region of interest of the human subject and/or the bone mineral density of the main region of interest of the human subject.

9. The system according to claim 1, wherein the processing unit is configured to determine a T-score based on the first detector signal, the scout image and/or the bone mineral density.

10. The system according to claim 1, wherein the processing unit is configured to determine, based on the first detector signal and/or the scout image, a lean soft tissue value and/or fat value.

11. The system according to claim 1, wherein the processing unit is configured to cause a warning signal, if the bone mineral density exceeds a predefined density threshold value or a predefined density threshold value range.

12. A method for CT imaging, comprising:
   a) Performing a scout scan of a scout region of interest of a human subject, such that a source for generating X-ray radiation is operated only with a first, single X-ray tube acceleration voltage to generates X-ray radiation during the scout scan, such that the respective X-ray radiation is transmitted through the scout region towards a detector for detecting X-ray radiation, wherein the detector detects simultaneously X-ray radiation of a first energy spectrum and of a different, second energy spectrum during the scout scan resulting in a first detector signal;
   b) Determining a scout image of the scout region of interest of the human subject based on the first detector signal of the detector caused by the scout scan;
   c) Performing a main scan of a main region of interest of a human subject subsequent to a) and/or b), such that the source is operated only with a second, single X-ray tube acceleration voltage to generates X-ray radiation during the main scan, such that the respective X-ray radiation is transmitted through the main region towards the detector, wherein the detector detects simultaneously X-ray radiation of the first energy spectrum and of the different, second energy spectrum during the main scan resulting in a second detector signal;
   d) Determining a main image of the main region of interest of the human subject based on the second detector signal of the detector caused by the main scan; and
   e) Determining a bone mineral density based on the first detector signal and/or the scout image.

13. The method according to claim 12, wherein step e) is performed at least partly parallel to step b), c) and/or d).

14. A non-transitory computer-readable medium for storing executable instructions, which when executed by at least one processor, cause the at least one processor to perform a method for CT imaging, the method comprising:
   a) performing a scout scan of a scout region of interest of a human subject, such that a source for generating X-ray radiation is operated only with a first, single X-ray tube acceleration voltage to generates X-ray radiation during the scout scan, such that the respective X-ray radiation is transmitted through the scout region towards a detector for detecting X-ray radiation, wherein the detector detects simultaneously X-ray radiation of a first energy spectrum and of a different, second energy spectrum during the scout scan resulting in a first detector signal;
   b) determining a scout image of the scout region of interest of the human subject based on the first detector signal of the detector caused by the scout scan;
   c) performing a main scan of a main region of interest of a human subject subsequent to a) and/or b), such that the source is operated only with a second, single X-ray tube acceleration voltage to generates X-ray radiation during the main scan, such that the respective X-ray radiation is transmitted through the main region towards the detector, wherein the detector detects simultaneously X-ray radiation of the first energy spectrum and of the different, second energy spectrum during the main scan resulting in a second detector signal;
   d) determining a main image of the main region of interest of the human subject based on the second detector signal of the detector caused by the main scan; and
   e) determining a bone mineral density based on the first detector signal and/or the scout image.

* * * * *